(12) United States Patent
Ou-Yang et al.

(10) Patent No.: US 10,314,478 B2
(45) Date of Patent: Jun. 11, 2019

(54) SYSTEM AND METHOD FOR MEASURING MICROFLUCTUATION OF ACCOMMODATION

(71) Applicant: National Chiao Tung University, Hsinchu (TW)

(72) Inventors: Mang Ou-Yang, Hsinchu (TW); Jin-Chern Chiou, Hsinchu (TW); Ting-Wei Huang, Hsinchu (TW); Yi-Chun Tsai, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 258 days.

(21) Appl. No.: 15/217,235

(22) Filed: Jul. 22, 2016

(65) Prior Publication Data

US 2017/0020386 A1    Jan. 26, 2017

(30) Foreign Application Priority Data

Jul. 22, 2015 (TW) .............................. 104123787 A

(51) Int. Cl.

| | |
|---|---|
| *A61B 3/09* | (2006.01) |
| *A61B 5/0488* | (2006.01) |
| *A61B 3/10* | (2006.01) |
| *A61B 5/00* | (2006.01) |
| A61B 5/0476 | (2006.01) |
| A61B 5/04 | (2006.01) |
| A61B 5/16 | (2006.01) |

(52) U.S. Cl.
CPC .................. *A61B 3/09* (2013.01); *A61B 3/10* (2013.01); *A61B 5/0488* (2013.01); *A61B 5/6821* (2013.01); A61B 5/04012 (2013.01); A61B 5/0476 (2013.01); A61B 5/16 (2013.01); A61B 5/6803 (2013.01)

(58) Field of Classification Search
CPC ........ A61B 3/09; A61B 5/0488; A61B 5/6821
USPC ......................................................... 600/546
See application file for complete search history.

(56) References Cited

U.S. PATENT DOCUMENTS

| | | | | |
|---|---|---|---|---|
| 2009/0105817 | A1* | 4/2009 | Bretthauer ............. | A61B 3/113 623/4.1 |
| 2014/0022505 | A1* | 1/2014 | Pugh .................... | A61B 5/6821 351/159.03 |
| 2015/0035745 | A1* | 2/2015 | Ou-Yang ................ | G06F 3/013 345/156 |
| 2015/0351690 | A1* | 12/2015 | Toth ..................... | A61B 5/6833 600/373 |

(Continued)

*Primary Examiner* — Daniel L Cerioni
(74) *Attorney, Agent, or Firm* — Muncy, Geissler, Olds & Lowe, P.C.

(57) ABSTRACT

A system for measuring microfluctuation of accommodation comprises a measuring module and a processing module. The measuring module includes at least one first sensing element attached to the area around an eye of a testee for measuring an EMG signal. The processing module is coupled with the measuring module for picking up a specific frequency range of the EMG signal as a measurement index of microfluctuation of accommodation, wherein the specific frequency range is between 0.1 Hz and 100 Hz. The system allows the testee to be tested in an open field of view and exempts the testee from experiencing fatigue in the muscle around the eyes. The system is compact and convenient to carry. A method for measuring microfluctuation of accommodation is also disclosed.

8 Claims, 2 Drawing Sheets

(56) References Cited

U.S. PATENT DOCUMENTS

2017/0188896 A1* 7/2017 Guth .................. G02C 7/083

* cited by examiner

SYSTEM AND METHOD FOR MEASURING MICROFLUCTUATION OF ACCOMMODATION

BACKGROUND OF THE INVENTION

1. Field of the Invention

The present invention relates to a system and method for measuring physiological information, particularly to a system and method for measuring accommodative fluctuation.

2. Description of the Prior Art

Eyes can reflect physiological states of human beings, such as fatigue, emotions (happiness, angry and sadness), and whether one is lying. Therefore, the fields concerned have gradually paid attention to the technology for measuring microfluctuation of accommodation. The conventional methods for measuring microfluctuation of accommodation are mainly based on optics or ultrasonics. In the conventional technologies, a testee gazes at an object at a specified distance or of a special type in a dark field of a limited space, and the variation of the eye lens of the testee is measured as an index of microfluctuation of accommodation.

However, the abovementioned measurement method is likely to fatigue the ciliary muscle because it demands the testee to gaze at a specified object at a near distance. Therefore, the conventional method may generate incorrect physiological information. Besides, the equipment used by the conventional method is bulky, inconvenient to carry, and hard to apply to clinical research.

Hence, the fields concerned are eager to develop an microfluctuation of accommodation measurement method to exempt the testee from ocular fatigue and reduce the volume of the measurement equipment.

SUMMARY OF THE INVENTION

The present invention proposes a system and method for measuring microfluctuation of accommodation, which directly measures the electromyograph (EMG) signal from the area around of an eye as a measurement index of microfluctuation of accommodation, wherein the measurement is undertaken in an open field of view, whereby the measurement is less likely to cause fatigue in the muscle around the eyes. Further, the system for measuring microfluctuation of accommodation is relatively compact, convenient to carry, and favorable to clinical application.

In one embodiment, the system for measuring microfluctuation of accommodation comprises a measuring module and a processing module. The measuring module includes at least one first sensing element, which are to be attached to the area around the eye of a testee for measuring an EMG signal. The processing module is coupled with the measuring module, picking up a specified frequency range of the EMG signal as a measurement index of microfluctuation of accommodation, wherein the specified frequency range is 0.1-100 Hz.

In one embodiment, the method for measuring microfluctuation of accommodation comprises steps: attaching at least one first sensing element to the area around the eye of a testee for measuring an EMG signal; and using a processing module to pick up a specified frequency range of the EMG signal as a measurement index of microfluctuation of accommodation, wherein the specified frequency range is 0.1-100 Hz.

Below, embodiments are described in detail in cooperation with the attached drawings to make easily understood the objectives, technical contents, characteristics and accomplishments of the present invention.

DESCRIPTION OF THE PREFERRED EMBODIMENTS

Figure 1:
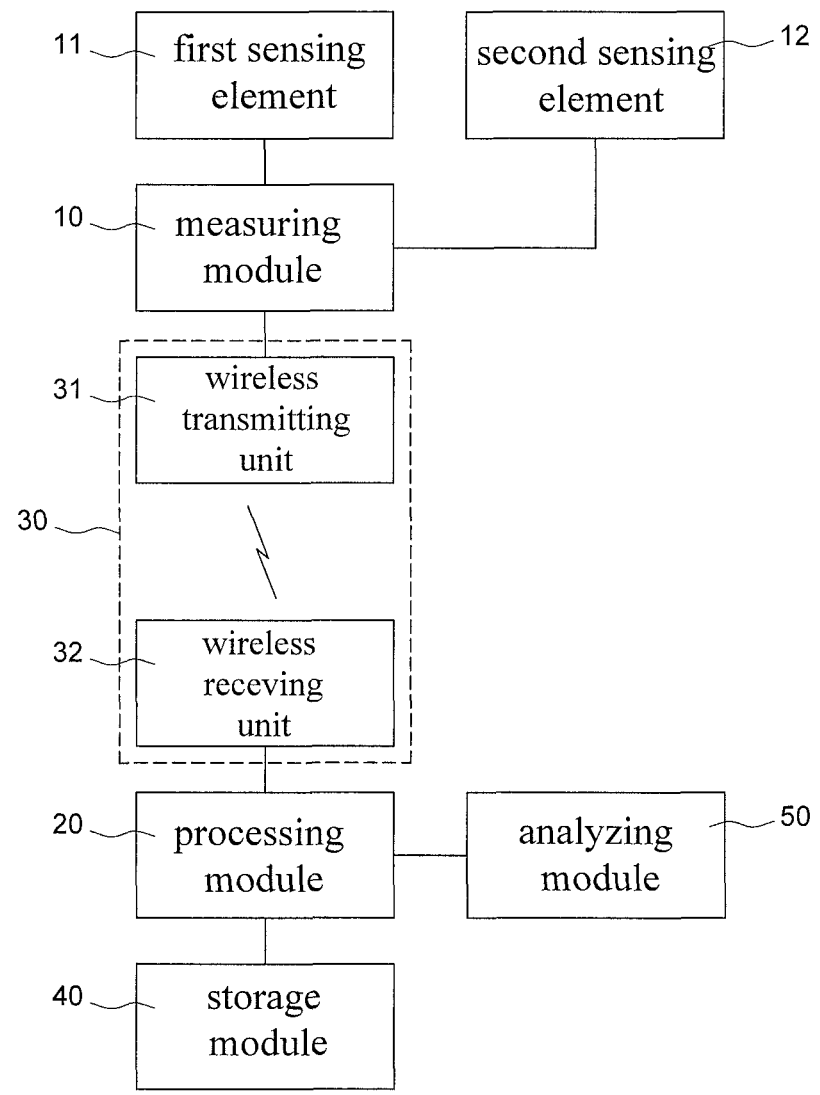
FIG. 1 is a block diagram schematically showing a system for measuring microfluctuation of accommodation according to one embodiment of the present invention.

The present invention will be described in detail with embodiments and attached drawings below. However, these embodiments are only to exemplify the present invention but not to limit the scope of the present invention. In addition to the embodiments described in the specification, the present invention also applies to other embodiments. Further, any modification, variation, or substitution, which can be easily made by the persons skilled in that art according to the embodiment of the present invention, is to be also included within the scope of the present invention, which is based on the claims stated below. Although many special details are provided herein to make the readers more fully understand the present invention, the present invention can still be practiced under a condition that these special details are partially or completely omitted. Besides, the elements or steps, which are well known by the persons skilled in the art, are not described herein lest the present invention be limited unnecessarily. Similar or identical elements are denoted with similar or identical symbols in the drawings. It should be noted: the drawings are only to depict the present invention schematically but not to show the real dimensions or quantities of the present invention. Besides, matterless details are not necessarily depicted in the drawings to achieve conciseness of the drawings.

Refer to FIG. 1. In one embodiment, the system for measuring accommodative fluctuation comprises a measuring module 10 and a processing module 20. The measuring module 10 includes at least one first sensing element 11. The first sensing element 11 is attached to the area around an eye of a testee for measuring an electromyograph (EMG) signal from the muscle around the eye (such as the ciliary muscle). It is easily understood: the measuring module 10 includes conventional front-end signal processing elements, such as amplifiers and filters. In one embodiment, the first sensing element 11 is an attachable electrode or an adhesive electrode pad. The processing module 20 is coupled with the measuring module 10 for picking up a specified frequency range of the EMG signal as a measurement index of microfluctuation of accommodation. The range of the frequency of the signal of microfluctuation of accommodation is far greater than that required for obtaining the physiological signals from the area around the eye, such as the signals of eyeball rotation, eye blinking, swallows, and respirations. Therefore, a specified frequency range of the EMG signal is picked up as a measurement index of microfluctuation of accommodation and used as the basic data for the succeeding analysis. In one embodiment, the specified frequency range is 0.1-100 Hz, preferably 0.5-50 Hz.

In one embodiment, the EMG signal measured by the measuring module 10 is transmitted to the processing module 20 in a wired way or a wireless way. In one embodiment, the system for measuring accommodative module of the present invention further comprises a wireless communication module 30 arranged between the measuring module 10 and the processing module 20. The wireless communication module 30 transmits the EMG signal measured by the measuring module 10 to the processing module 20 in a wireless way. In one embodiment, the wireless communication module 30 includes a wireless transmitting unit 31 and a wireless receiving unit 32. The wireless transmitting unit 31 is electrically connected with the measuring module 10, and the wireless receiving module 32 is electrically connected with the processing module 20, whereby the EMG signal measured by the measuring module 10 can be wirelessly transmitted to the processing module 20.

In one embodiment, the system for measuring accommodative module of the present invention further comprises a storage module 40 electrically connected with the processing module 20. The storage module 40 can store the measurement index of microfluctuation of accommodation, i.e. a specified frequency range of the EMG signal, which is to be further processed to evaluate the physiological states of the testee. In one embodiment, the storage module 40 is a hard disc, a flash memory, or an optical disc.

In one embodiment, the system for measuring accommodative module of the present invention further comprises an analyzing unit 50 coupled with the processing module 20. The analyzing unit 50 can analyze the measurement index of microfluctuation of accommodation, i.e. a specified frequency range of the EMG signal, to evaluate the physiological states of the testee, such as fatigue, emotions (happiness, angry and sadness), and whether one is lying. In one embodiment, the measuring module 10 also includes a second sensing element 12. The second sensing element 12 may be arranged near the head of the testee to receive an electroencephalograph (EEG) signal that is related with the control of microfluctuation of accommodation, such as the electric potential variation of the brain cortex, which controls the ciliary muscle. Thereby, the analyzing unit 50 can simultaneously analyze the microfluctuation of accommodation-related EMG signal and the microfluctuation of accommodation-related EEG signal to evaluate the physiological states of the testee. In one embodiment, the system for measuring microfluctuation of accommodation of the present invention further comprises a head-wearing element, such a pair of glasses, a scarf, a cap, or a headgear. The sensing module 10 (including the first sensing element 11 and the second sensing element 12) is disposed in the head-wearing element to measure in realtime the EMG signal from the area around the eye of the testee and/or the EEG signal of the testee.

It should be noted: the configurations of the abovementioned elements in different designs may not be the same. For example, the processing module 10 is disposed in a computer, a mobile Internet access device, a portable device, or a far-end server; the measuring module 10 transmits an unprocessed EMG signal to one of the abovementioned external electronic devices in a wired or wireless way, and the external electronic device picks up the required EMG signal for analysis. Alternatively, the measuring module 10 and the processing module 20 are integrated in a single electronic device, and the electronic device transmits the measurement index of microfluctuation of accommodation, i.e. a specified frequency range of the EMG signal, to one of the abovementioned external electronic devices so that external electronic device whose computation capability is more powerful can undertake faster and more precision analysis.

Via the abovementioned technical scheme, the system for measuring microfluctuation of accommodation can directly measure an EMG signal from the muscle around an eye of a testee. Therefore, the testee is tested in an open field of view. In other words, the distance between the testee and the object the testee gazes at is larger in the present invention than in the conventional optics or ultrasonics-based technology. Then, the testee using the present invention is less likely to experience ocular fatigue than the testee using the conventional device. No matter whether the distance or the type of the object is varied, it would cause visual accommodation. In other words, the variation of the distance to the object or the variation of the picture of the television would cause the variation of the EMG signal of the muscle around the eye of the testee. Thus, the system of the present invention can detect the variation of the distance or the picture via measuring the EMG signal. The present invention can apply to a further wider field than the conventional technology.

Figure 2:
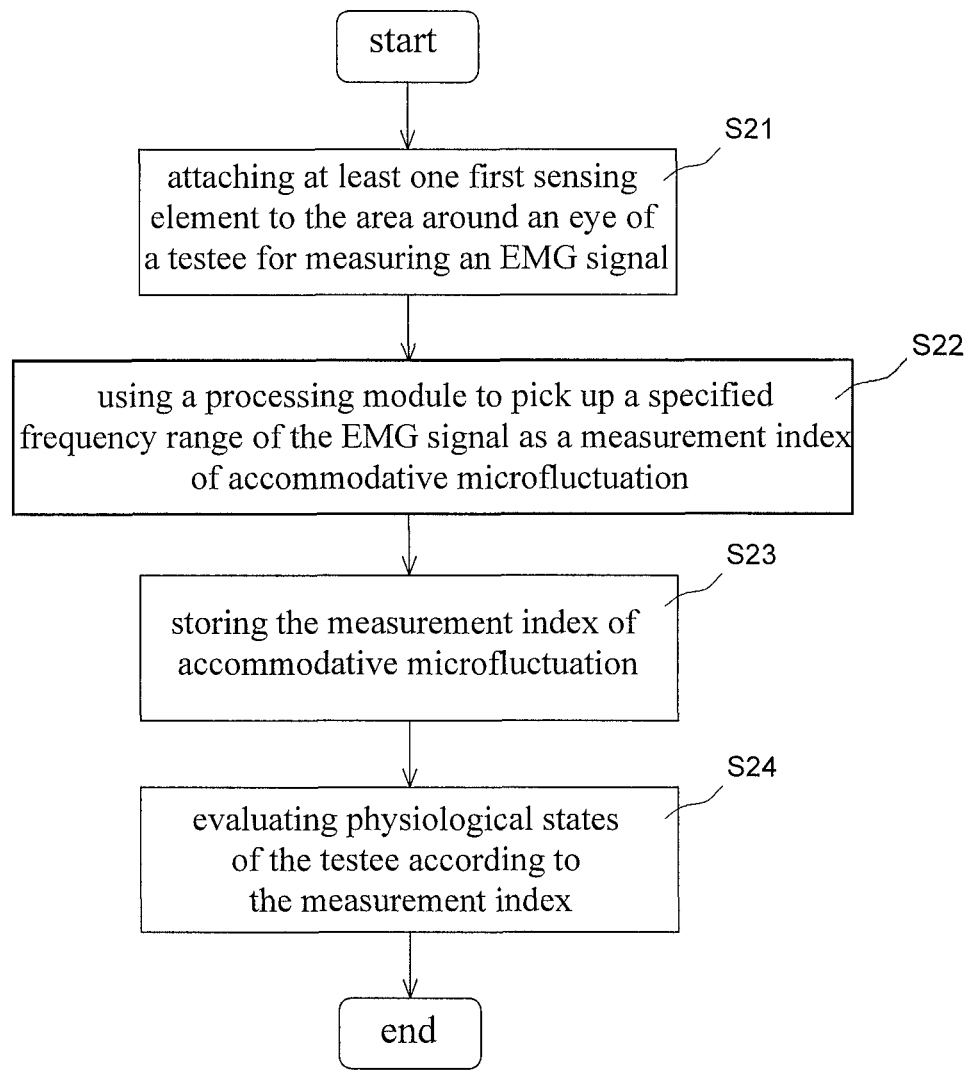
FIG. 2 is a flowchart of a method for measuring microfluctuation of accommodation according to one embodiment of the present invention.

Refer to FIG. 2. In one embodiment, the method for measuring accommodative fluctuation comprises Steps S21-S24. In Step S21, attach at least one first sensing element to the area around an eye of a testee for measuring an EMG signal. In Step S22, use a processing module to pick up a specified frequency range of the EMG signal as a measurement index of microfluctuation of accommodation, wherein the specified frequency range is 0.1-100 Hz.

In Step S23, the processing module stores the processed measurement index of microfluctuation of accommodation in a storage module. In Step S24, the processing module or an external electronic device analyzes the measurement index to evaluate the physiological states of the testee. In one embodiment, the method for measuring microfluctuation of accommodation of the present invention further uses at least one second sensing element to measure an EEG signal, whereby the processing module or the external electronic device can evaluate the physiological states of the testee via analyzing the measurement index and the EEG signal. The details thereof have been described hereinbefore and will not repeat herein.

In conclusion, the system and method for measuring microfluctuation of accommodation directly measures the EMG signal from the area around an eye of a testee as a measurement index. In the present invention, the testee is tested in an open field of view and exempted from fatigue in the muscle around the eyes. Further, as the system for measuring microfluctuation of accommodation of the present invention neither uses complicated optical elements nor adopts complicated design, it is compact, convenient to carry, favorable to clinical application.

What is claimed is:

1. A system for measuring microfluctuation of accommodation, comprising:
   a measuring module including at least one first sensing element configured to attach to an area around an eye of a testee for measuring an electromyograph (EMG) signal; and
   a processing module coupled with said measuring module and picking up a specified frequency range of said EMG signal as a measurement index of microfluctuation of accommodation, wherein said specified frequency range is 0.1-100 Hz.

2. The system for measuring microfluctuation of accommodation according to claim 1 further comprising:
   a storage module electrically connected with said processing module and storing said measurement index.

3. The system for measuring microfluctuation of accommodation according to claim 1 further comprising:
   a wireless communication module arranged between said measuring module and said processing module, and wirelessly transmitting said EMG signal from said measuring module to said processing module, wherein said wireless communication module comprises a wireless transmitting unit electrically connected with said measuring module and a wireless receiving unit electrically connected with said processing module.

4. The system for measuring microfluctuation of accommodation according to claim 1, wherein said specified frequency range is 0.5-50 Hz.

5. The system for measuring microfluctuation of accommodation according to claim 1 further comprising:
   a head-wearing element, wherein said measuring module is arranged inside said head-wearing element.

6. The system for measuring microfluctuation of accommodation according to claim 1, wherein said first sensing element is an attachable electrode or an adhesive electrode pad.

7. The system for measuring microfluctuation of accommodation according to claim 1, wherein said processing module is arranged in a computer, a mobile Internet-access device, a portable device, or a far-end server.

8. The system for measuring microfluctuation of accommodation according to claim 1, wherein said measuring module and said processing module are integrated in a single electronic device.

\* \* \* \* \*